United States Patent [19]

Anthon

[11] Patent Number: 4,659,933

[45] Date of Patent: Apr. 21, 1987

[54] SURFACE ANALYZER AND METHOD

[75] Inventor: Erik W. Anthon, Santa Rosa, Calif.

[73] Assignee: Optical Coating Laboratory, Inc., Santa Rosa, Calif.

[21] Appl. No.: 784,211

[22] Filed: Oct. 4, 1985

Related U.S. Application Data

[63] Continuation of Ser. No. 556,618, Nov. 28, 1983, abandoned.

[51] Int. Cl.[4] .................... G01N 21/47; G01N 21/55
[52] U.S. Cl. .................... 250/372; 356/446; 356/448; 250/358.1
[58] Field of Search .............. 250/372, 358.1, 359.1, 250/504 R, 505.1; 356/445, 446, 448

[56] References Cited

U.S. PATENT DOCUMENTS

| | | | |
|---|---|---|---|
| 2,315,282 | 3/1943 | Snow | 356/448 |
| 2,735,017 | 2/1956 | Beard et al. | 250/372 |
| 3,591,291 | 7/1971 | Greer et al. | 356/371 |
| 3,960,077 | 6/1976 | Aylett | 356/448 |
| 3,999,864 | 12/1976 | Mutter | 356/448 |
| 4,245,217 | 1/1981 | Steinhage | 250/505.1 |
| 4,352,017 | 9/1982 | Duffy et al. | 250/372 |
| 4,364,663 | 12/1982 | Gardner et al. | 356/371 |
| 4,511,800 | 4/1985 | Harbeke et al. | 250/372 |

FOREIGN PATENT DOCUMENTS 815492  3/1981  U.S.S.R. ............... 356/371

Primary Examiner—Carolyn E. Fields
Attorney, Agent, or Firm—Flehr, Hohbach, Test, Albritton & Herbert

[57] ABSTRACT

An analyzer for analyzing the surface of an object which is substantially opaque to ultraviolet light. The analyzer includes a substantially light-tight housing having an aperture therein for viewing the surface of the object to be analyzed. An illuminator is carried by the housing and includes a source of ultraviolet light and an optical imaging device for directing light from the source through the aperture and onto the surface of the object to illuminate the surface of the object. A collector is carried by the housing including a sensor responsive to ultraviolet light and an optical imaging device for receiving ultraviolet light from the surface through the aperture and directing it onto the sensor. A tilting mechanism is carried by the housing and permits relative tilting movement between the surface of the object and the housing whereby substantially only scattered energy is collected in one position of the housing and substantially only specularly reflected energy is collected in a second position of the housing.

27 Claims, 8 Drawing Figures

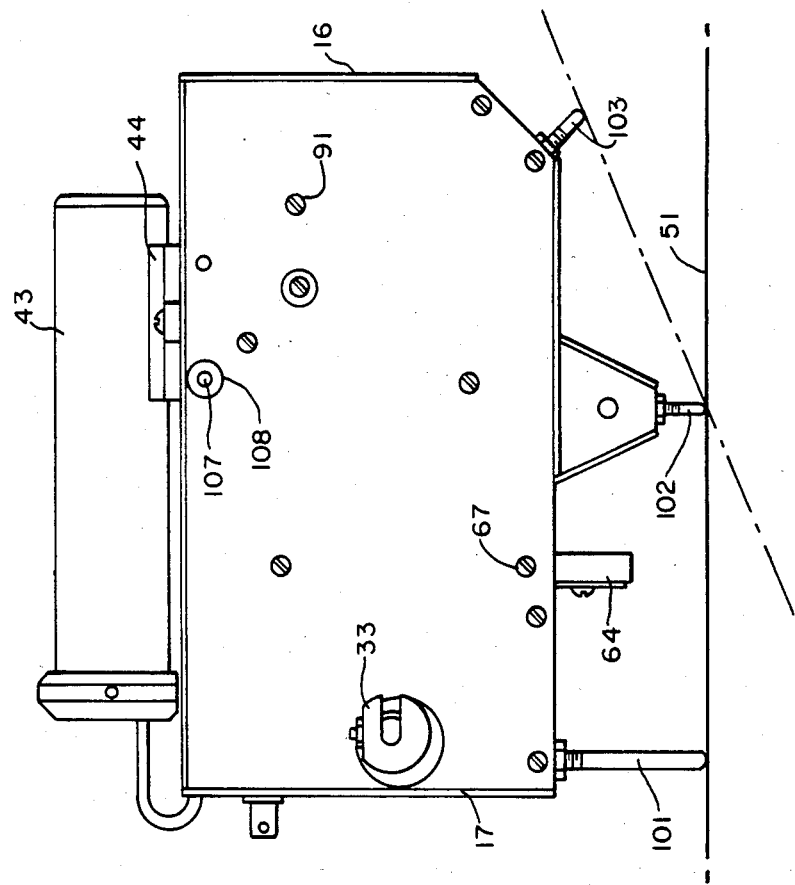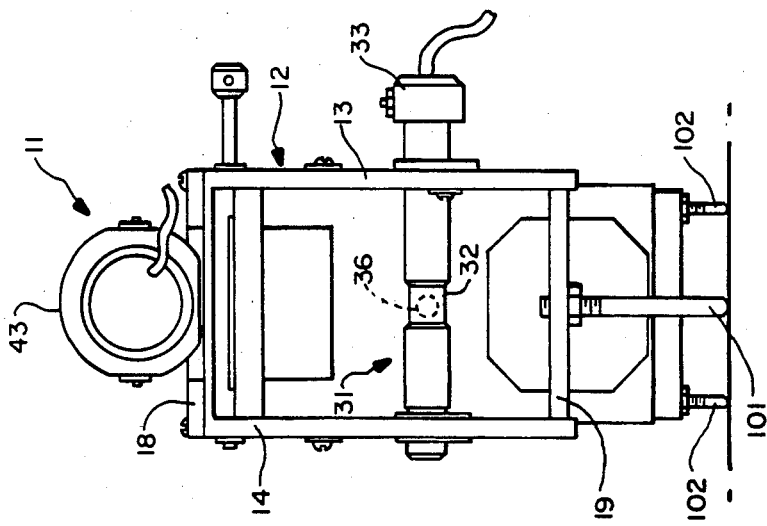

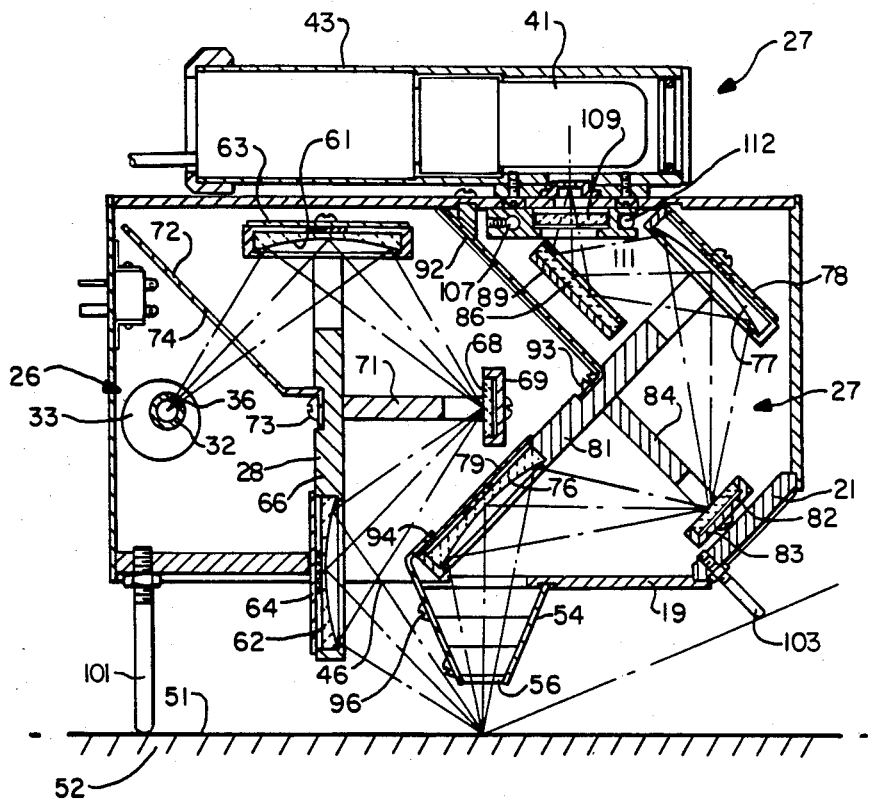
FIG. —3
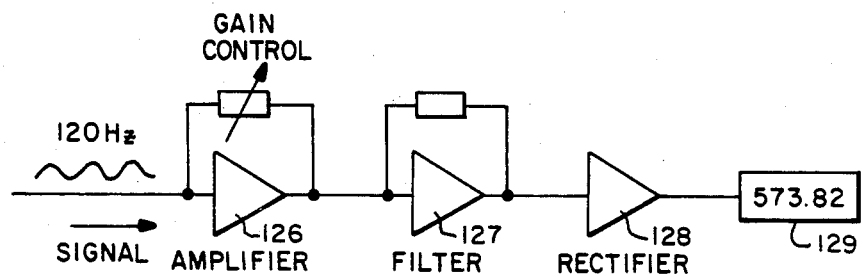
FIG. —4

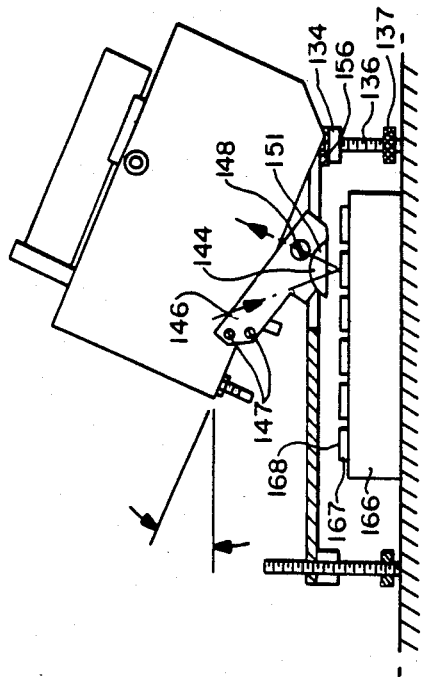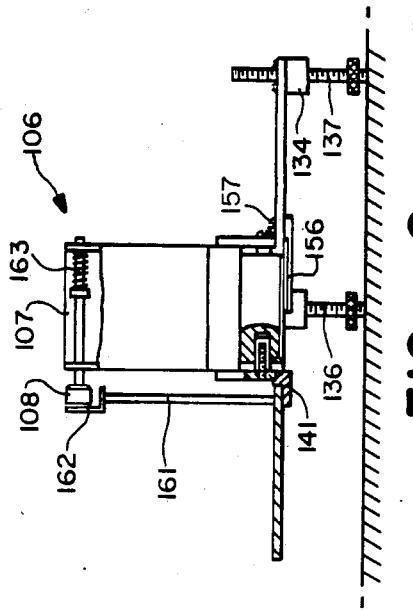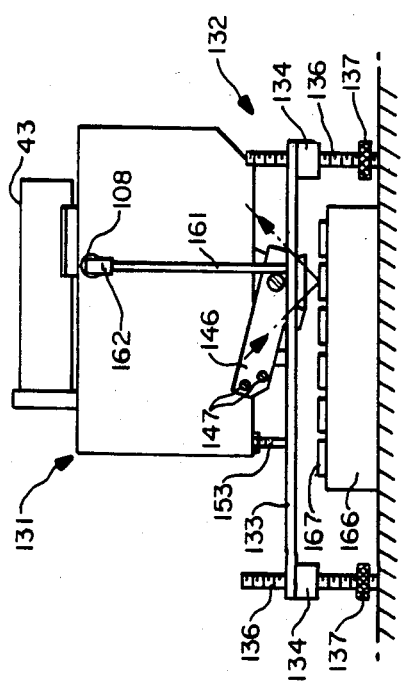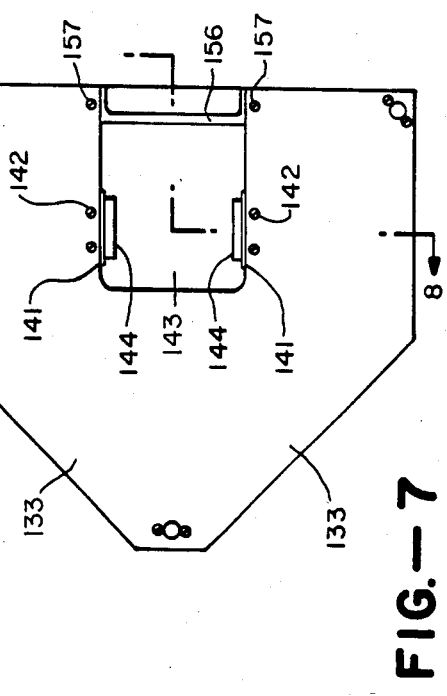

SURFACE ANALYZER AND METHOD

This is a continuation of application Ser. No. 556,618 filed Nov. 28, 1983, now abandoned.

This invention relates to a surface analyzer and method utilizing ultraviolet light for measuring scattered energy and specularly reflected energy.

In the past it has been the practice of opticians to observe the degree of perfection of a surface by visually observing the amount of light scattered by the surface. Such visual observations have been found to be inadequate for precision optical components such as used in connection with lasers and laser gyroscopes. There is therefore a need for an apparatus and method making possible the evaluation of surface characteristics of optical components.

In general it is an object of the present invention to provide a surface analyzer and method which characterizes a surface by reflected scatter of ultraviolet light.

Another object of the invention is to provide an analyzer and method of the above character in which reflective optical elements are utilized.

Another object of the invention is to provide an analyzer and method of the above character in which a plurality of optical elements are utilized in a series to filter out unwanted light.

Another object of the invention is to provide a surface analyzer of the above character which can be moved between calibrate and measure positions.

Additional objects and features of the invention will appear from the following description in which the preferred embodiments are set forth in detail in conjunction with the accompanying drawings.

FIG. 1 is a front elevational view of a surface analyzer incorporating the present invention.

FIG. 2 is a side elevational view of a surface analyzer incorporating the present invention taken along the line 2—2 of FIG. 1.

FIG. 3 is a cross sectional view in side elevation of the surface analyzer shown in FIGS. 1 and 2.

FIG. 4 is a schematic block diagram of the electronic circuitry used in the surface analyzer.

FIG. 5 is a side elevational view of another embodiment of a surface analyzer incorporating the present invention shown in a "measure" position.

FIG. 6 is a view similar to FIG. 5 but showing the surface analyzer in a "calibrate" position.

FIG. 7 is a top plan view of the stand which is utilized in the embodiment shown in FIGS. 5 and 6.

FIG. 8 is a cross sectional view taken along the line 8—8 of FIG. 7.

In general, the surface analyzer is used for analyzing the surface of an object which is substantially opaque to ultraviolet light. A substantially light-tight housing is provided which has aperture means therein for viewing the surface of the object. Illuminator means is carried by the housing and includes a source of ultraviolet light and optical imaging means for directing light from the source through the aperture and onto the surface of the object to illuminate the surface of the object. Collector means is carried by the housing and includes means responsive to ultraviolet light and optical imaging means for receiving through the aperture means reflected ultraviolet light from said surface and directing it onto the means responsive to the ultraviolet light. Means is carried by the housing permitting relative tilting between first and second positions between the surface of the object and the illuminator means and the collector means whereby substantially only reflected scattered energy is collected in said one position and substantially only specularly reflected energy is collected in said second position.

More particularly as shown on the drawings, two embodiments are particularly disclosed. One embodiment shown in FIGS. 1 through 5 is one which can rest upon the surface to be analyzed. The other embodiment which is shown in FIGS. 6 and 7 is one which is self-supported and does not rest upon the surface to be analyzed but overlies that surface.

The surface analyzer 11 shown in FIGS. 1 through 5 consists of light-type box-like housing or case 12. By way of example, the box can have dimensions of 9 inches by 5 inches with a width or depth of $3\frac{1}{2}$ inches. The housing 12 consists of parallel spaced apart side walls 13 and 14, parallel and spaced apart front and rear walls 16 and 17 and spaced apart and parallel top and bottom walls 18 and 19. Inclined wall 21 is also provided which adjoins the bottom wall 19 and the front wall 16.

Illuminator means 26 and collector means 27 are carried by the housing. The illuminator means 26 and the collector means 27 include substantially identical optical subassemblies 28 and 29. The optical subassemblies are mounted within the light-tight housing and each are separated in the housing so that they are light-tight from each other in a manner hereinafter described.

The illuminator means 26 consists of a source 31 of ultraviolet light of a conventional type. For example, a low pressure mercury vapor lamp 32 can be utilized which has approximately 90% of its emission at 254.7 nanometers. The lamp 32 is mounted in a lamp housing 33 which is disposed in the side walls of the housing or case 12 near the rear extremity of the case. The lamp housing 33 is mounted in the side walls by the use of eccentric plugs 34 to permit precision positioning of the lamp 32. The housing 33 is provided with an aperture 36 through which the ultraviolet light from the lamp 32 can pass. The lamp 32 is operated on alternating current. Therefore it turns off and reignites at each half cycle of current. The light output from the lamp is therefore modulated at 120 Hertz just as if it had been chopped. The optical subassemblies 28 and 29 are designed so that they will transmit only the 253.7 nanometer energy. No energy, especially shorter wavelengths should reach the surface to be illuminated. This is particularly important because radiation of 189 nanometers, some of which is produced by the lamp could produce fluorescence in the 250 nanometer region.

The collector means 27 includes a detector 41 which is in the form of a solar blind photomultiplier tube of a conventional type which has a spectral range from 160 to 320 nanometers. The tube should be very sensitive to 253.7 nanometers even though it can have the ability to sense some other wavelengths. The photomultiplier which forms the detector 41 is mounted in a cylindrical housing 43 mounted on the top wall 18 by the use of a bracket 44. The high voltage which is required for operation of the photomultiplier tube is obtained from a miniature power supply which is integrally mounted within the tube socket. The sensitivity of the photomultiplier tube can be varied by adjusting the high voltage level which can be varied from 400 to 900 volts by use of an external variable resistor (not shown).

No energy especially of longer wavelengths should reach the detector 41 from the illuminated sample area.

Radiation of 253.7 nanometers will produce fluorescence in many cases. The fluorescence can be mistaken for scatter but it will always be of a significantly longer wavelength than that of the illuminating light. Thus, the optical assemblies 28 and 29 which are utilized in the illuminator means 26 and the collector means 27 all utilize reflective optics and the reflective surfaces are coated with a long wave pass edge filters for preferential reflectance of 253.7 nanometers and much lower reflectance for longer wavelengths.

Both the illuminator means 26 and the collector means 27 utilize optical subassemblies 28 and 29 which are imaging systems focused at the same point, i.e., the working point of the test surface. In the arrangement shown the axes of the two optical systems are 45° apart. The imaging in each of the subassembly is accomplished by two concave spherical mirrors used at an angle of incidence of 45°. As shown, the illuminator means projects ultraviolet light through an aperture 46 in the bottom wall 19 of the housing or case 12 onto surface 51 of an object or structure 52 such as one formed of glass or any other material, the surface of which it is desired to analyze and which is relatively opaque to ultraviolet light. A conical structure 54 is mounted on the bottom wall 19 of the case 12 and is provided with an opening 56 through which light energy reflected from the surface 51 can pass after which it is imaged by the optical subassembly 29 onto a small aperture 57 next to the photomultiplier tube 41.

The optical subassembly 28 consists of two concave spherical mirrors 61 and 62 which are used at 45° angles of incidence. The mirrors 61 and 62 are carried by brackets 63 and 64. The brackets 63 and 64 are mounted upon a member 66 within the housing or case 12 and which is secured to the side walls 13 and 14 by screws 67. Another mirror 68 is provided of a planar type which is adapted to receive reflected energy from the mirror 61 and to direct the same onto the mirror 62. The mirror 68 is carried in a bracket 69. The bracket 69 is secured to a post 71 extending outwardly at right angles to the member 66. A light baffle 72 is also mounted upon the member 66 by a screw 73. As shown in FIG. 3, this baffle extends upwardly and outwardly from the center of the member 66 and is provided with an opening 74 through which light from the lamp 32 can pass. The light impinges upon the mirror 61 and thence to the mirror 68 and thence to the mirror 62 after which the light energy is reflected through the aperture 46 in the housing or case 12 to illuminate the surface 51 to be examined.

Similarly, the optical subassembly 29 consists of first and second concave spherical mirrors 76 and 77. The mirrors 76 and 77 are mounted within brackets 78 and 79. The brackets 78 and 79 are mounted upon a member 81 which extends diagonally of the housing case 12 and is secured to the side walls 13 and 14 of the case by suitable means such as screws 82. Another planar mirror 83 is carried by a bracket 84. The bracket 84 is secured to the member 81.

The baffle 72 limits stray light from the source 32. Another planar mirror 86 is provided as a part of the subassembly 29 and receives energy reflected from the mirror 77. The mirror 86 is carried by a bracket 89 which is secured to the side walls 13 and 14 of the housing by screws 91. Thus it can be seen from FIG. 3, light reflected from the surface 51 passes through an opening 56 in the conical structure 54 and impinges upon the mirror 76 which reflects the same onto the mirror 82 after which it is reflected onto the mirror 77 after which it is reflected onto the mirror 86 and after which it is reflected through the aperture 57 onto the photomultiplier tube 41.

A light baffle 92 is provided which has one end secured to the member 81 by suitable means such as a screw 93. Another light baffle 94 secured to the conical structure 54 by screws 96 assures that the subassembly 28 will be optically tight with respect to the optical subassembly 29.

As is well known to those skilled in the art, a spherical mirror used at a 45° angle of incidence provides large amounts of astigmatism. In fact, the focal length in the incidence plane of the mirror is half of the focal length in the plane perpendicular to the incidence plane. The result of this is that an intermediate image is formed between the two concave mirrors in the incidence plane while the beam will be collimated between the two concave mirrors in a plane perpendicular to the incidence plane. For this reason no intermediate image is formed in this plane. The effect of the astigmatism of the mirrors is therefore eliminated as far as imaging through the system of the present invention is concerned.

The optical system in the subassemblies is folded between the two concave mirrors by a flat mirror at a 45° angle of incidence. A substantial amount of coma in the spherical mirrors at 45° is also present. The relative orientation of the two concave mirrors is chosen so that the combined coma of the two mirrors substantially cancel out.

The resulting imaging provided by the optical subassemblies 28 and 29 has a numerical aperture of 0.2 in the plane of incidence and 0.3 in the plane perpendicular to the incidence plane. The imaging is reasonably sharp with a blur spot less than 1 millimeter in diameter. As can be seen, the two optical subassemblies 28 and 29 are nested into each other. The collector subassembly 29 has an extra folding mirror 86 with 45° incidence between the second concave mirror 77 and the receiving aperture 57.

The light energy emitted from the lamp 32 enters the optical subassembly 28 through the aperture 36 which can be of a suitable size such as four millimeters in diameter in the shroud or housing 33 which surrounds the lamp. The optical system images the light from the lamp onto an illuminated spot on an area of the surface slightly larger than the 4 millimeters of the aperture. The receiving aperture 57 of the collector means 27 can be of a suitable size such as 1.5 millimeters. The size of this aperture can be readily changed by using different inserts. The signal level that can be obtained through a 1.5 millimeter aperture is more than adequate. The usefulness of smaller apertures, however, would be limited by the imaging qualities of the optical system utilized. The scattered or reflected energy from an area only slightly larger than 1.5 millimeters in diameter within the illuminated area collected by the collecting optics.

With respect to the optical subassemblies 28 and 29, it is important that both transmit only the 253.7 nanometer energy. No energy especially of the shorter wavelength should reach the illuminated surface 51. As pointed out earlier, the reflective optics utilized in the subassemblies 28 and 29 are coated with a long wave pass edge filter of a type well known to those skilled in the art for preferential reflectance of 253.7 nanometers and much lower reflectance for longer wavelengths. All of the reflected surfaces are designed to operate at or near a 45° angle of incidence and all surfaces are coated with quarterwave stacks at 253.7 nanometers designed for 45° incidence angles.

The illuminating optical subassembly 28 has three, and the collective optical subassembly 29 has four reflective surfaces in series. This provides extremely good filtering for unwanted light. A reflectivity as high as 10% per reflector would turn into 0.01% after four reflections. Only energy within the real high reflectance region of the coating can therefore be carried through the system. In this case, only light of 253.7 nanometers will be detected. The coatings can be of a conventional type. They can consist of a plurality of pairs as, for example, in excess of ten of silica and scandium oxide.

Tilting means is carried by the housing 12 permitting relative tilting movement between first and second positions between the housing 12 and the surface to be analyzed, namely from a vertical position to a tilted forward position by suitable angle such as $22\frac{1}{2}°$. The $22\frac{1}{2}°$ angle for movement of the housing between first and second positions has been selected because the angle between the illuminating beam and the detected beam is 45°. The detected beam is normally perpendicular to the test surface and tilting the housing by $22\frac{1}{2}°$ centers the reflectance of the test surface from the illuminating beam into the receiving beam so that there is a maximum light throughout. Such means consists of a rear support leg 101 which is mounted upon the bottom wall 19 and a pair of shorter legs 102 which are mounted on the lower extremity of the conical support structure 54 to in effect provide a three-legged support for supporting the housing or case 12 so that it is in a vertical or first position. Additional means in the form of a leg 103 is secured to the inclined wall 21 and also provides a three-legged means in conjunction with the legs 102 for supporting the housing or case 12 in a forward position where it is tilted at an angle of $22\frac{1}{2}°$ forward of the vertical position. As can be seen, the legs 101, 102 and 103 are adapted to engage the top surface 51 of the object 52 which is being analyzed.

A sliding filter assembly 106 is provided in the housing case 12 and is adapted to move into a filtering position when the housing 12 is moved into its forward or second position. The filter assembly 106 consists of a push or slide rod 107 which is slidably mounted in the side walls 13 and 14 of the case 12. The rod 107 is provided with a knurled knob 108 which is adapted to be grasped by the hand. An attenuation filter 109 is carried by a framework 111 which is enclosed within the housing or case and which has one end of the same carried by the rod 107. The other end of the framework 111 is slidably mounted upon a rod 112 mounted in the side walls 13 and 14 so that the attenuation filter 109 can be moved between first and second positions. In the first position it is in the beam and in the second position it is out of the beam. The attenuation filter 109 that is used with the specularly reflected beam should preferably attenuate all wavelengths. A thin perforated stainless steel screen is used. It has microscopic holes and transmits about 0.1%.

Operation and use of the surface analyzer in performing the method of the present invention can be described in conjunction with the block diagram in FIG. 4. Let it be assumed that it is desired to check the quality of a surface 51 of a relatively large area of an object 52 as, for example, glass or other material opaque to ultraviolet light. When such is the case, the instrument is placed directly upon the surface with the legs 101 and 102 resting upon the surface to support the same in a vertical position. As can be seen, the legs can be adjusted to position the housing or case 12 at a predetermined distance above the test surface as, for example, from 0.61 to 0.64 inches.

The surface analyzer is turned on and the mercury lamp 32 is warmed up. The attenuation filter 109 is retained in its out-of-the beam position. When the instrument is in a vertical or upright position as shown in FIGS. 1 and 2 of the drawing, only reflected scattered energy is collected. The scattered light which is collected is directed through the optical subassembly 29 onto the photomultiplier tube 41. The photomultiplier tube 41 provides a 120 Hertz electrical signal to the electronics in the block diagram shown in FIG. 4. The signal is supplied to an amplifier 126 which is provided with gain control. The output of the amplifier is supplied to a 120 Hertz filter 127 which preferentially filters the 120 Hertz and attenuates other frequencies. The signal is then supplied to a rectifier 128 which generates a DC voltage proportional to the amplitude of the AC signal and this signal is supplied to a digital volt meter 129 which provides a digital readout of the signal supplied from the photomultiplier tube 41. This reading gives an indication of the scattered light being reflected by the surface 51. When the instrument is tilted to a forward position so that the leg 103 is in engagement with the surface 51, specularly reflected energy will be collected. Since the specularly reflected energy is normally many times greater than that of the scattered energy, the attenuation filter is normally used and placed in the beam so as to prevent overloading of the photomultiplier tube 41. A signal is again supplied to the electronics giving a digital readout with respect to the specularly reflected energy which is collected by the instrument. This signal is used to calibrate the surface analyzer. When the analyzer has been calibrated, the housing is returned to the vertical position and the reflected scattered light is measured to give an indication of the surface quality. It can be seen that by using ultraviolet light, the ultraviolet light will only see the first surface of the glass substrate 52 and therefore the readings which are given by the instrument precisely define the quality of the first surface being examined.

Another embodiment of the surface analyzer is shown in FIGS. 5, 6, 7 and 8. As shown therein, the surface analyzer consists of a housing or case 131, which is constructed in a manner substantially identical to the housing or case 12 described in the previous embodiment. The housing or case 131 is mounted upon a stand 132. The stand 132 consists of a flat plate 133 which is generally rectangular as shown in FIG. 7 with two corner portions removed. Means is provided for supporting the plate 133 in an elevated position and consists of nuts 134 which are mounted on three corners of the plate. Three height adjusting screws 136 are threaded into the nuts 134 and extend vertically through the plate 133. The screws 136 are provided with knurled knobs 137 to facilitate adjustment of the screws whereby the plate 133 can be leveled into a horizontal position.

Means is provided for mounting the housing or case 131 upon the stand 132 to facilitate movement of the housing relative to the stand between first and second positions with the first position being a vertical position and the second position being a forward tilted position and consists of first and second members 141 which are secured to the plate 133 by screws 142. The members 141 are spaced apart and parallel and extend upwardly through a rectangular shaped opening 143 provided in the plate 133. The members 141 are formed with semi-cylindrical surfaces 144 (see FIG. 6). A pair of arms 146 are mounted on opposite sides of the housing or case 131 by screws 147 and 148. As shown in FIGS. 5 and 6, the arms 146 have their rear extremities secured to the rear extremity of the housing 131 and depend downwardly in a forward direction. The arms 146 are provided with circular cutouts 151 and are adapted to seat on the semi-cylindrical surfaces 144. This permits rotational or tilting movement of the housing 131 about a horizontal axis. The housing 131 is provided with a leg 153 which is adapted to seat upon the top of the plate 133 as shown in FIG. 5 and serves to retain the housing 131 in a vertical position. Means is provided for limiting the forward travel of the housing 131 when it is tilted so that the angle of tilt will be $22\frac{1}{2}°$. Such means consists of a cross member 156 secured to the plate by screws 157. The cross member 156 is adapted to be engaged by the housing or case 131 to arrest the forward tilt of the housing to the predetermined angle.

Means is carried by the stand 132 so as to retain the sliding filter assembly 106 in a predetermined position when the housing 131 is in a vertical position. This means consists of a vertical rod 161 which is secured to the plate 133 and which has an L-shaped spring member 162 mounted on the upper extremity of the same and adapted to engage the knob 108 of the push rod 107. The spring member 162 retains the push rod carrying the attenuation filter 109 in a position so that the filter is out of the light beam passing to the aperture 57 against the force of a spring 163 mounted on the rod 107. Thus it can be seen that when the housing 131 is moved to a forward tilting position, the knob 108 will be moved out of engagement with the spring member 162 to permit the spring 163 to move the push rod 107 into a position so that the attenuation filter 109 is moved into the light beam entering the aperture 57.

As shown in FIGS. 5 and 6, the stand 132 is constructed in such a manner so that the surfaces of the samples to be evaluated can be positioned below the stand. Thus there has been provided a block 166 having a plurality of substrates 167 mounted thereon which have surfaces 168 which are to be evaluated by the surface analyzer.

As shown in the previous embodiment, when the surface analyzer is in the tilted forward position, it is in the calibrate position and when it is in the horizontal or vertical position, it is in the measure position.

It is apparent from the foregoing that there has been a surface analyzer and method which utilizes ultraviolet light for measuring scattered energy and specularly reflected energy which will provide a digital output giving precise measurements of the surface characteristics being analyzed. The instrument has been constructed in such a manner so that it can make such measurements readily and rapidly.

What is claimed is:

1. In an analyzer for analyzing the surface of an object which is substantially opaque to ultraviolet light, a substantially light-tight housing having aperture means therein for viewing the surface of the object to be analyzed, illuminator means carried by the housing including a source of ultraviolet light and optical imaging means for directing light from the source through the aperture means and onto the surface of the object to illuminate the surface of the object, collector means carried by the housing including means responsive to ultraviolet light, optical imaging means for receiving ultraviolet light from said surface through said aperture means and directing it onto the means responsive to ultraviolet light and means carried by the housing permitting relative tilting movement between the surface of the object and the housing so that substantially only scattered reflected ultraviolet light is collected in one position of the housing and substantially only specularly reflected ultraviolet light is collected in a second position of the housing.

2. An analyzer as in claim 1 together with a stand overlying the surface of the object to be analyzed, the stand having an opening therein, and means mounting the housing on the stand permitting relative movement between the housing and the stand so that alternatively scattered reflected energy and specularly reflected energy are collected.

3. An analyzer as in claim 2 wherein said stand is formed with an opening therein through which the observed surface is analyzed.

4. In an analyzer for analyzing the surface of an object which is substantially opaque to ultraviolet light, a substantially light-tight housing having aperture means therein for viewing the surface of the object to be analyzed, illuminator means carried by the housing including a source of ultraviolet light and optical imaging means for directing light from the source through the aperture means and onto the surface of the object to illuminate the surface of the object, collector means carried by the housing including means responsive to ultraviolet light, optical imaging means for receiving ultraviolet light from said surface through said aperture means and directing it onto the means responsive to ultraviolet light, means carried by the housing permitting relative tilting movement between the surface of the object and the housing so that substantially only scattered reflected ultraviolet light is collected in one position of the housing and substantially only specularly reflected ultraviolet light is collected in a second position of the housing and attenuator means mounted in the housing and movable between a position in which it is in the light beam received by the means responsive to the ultraviolet light and a position out of the beam received by the means responsive to the ultraviolet light.

5. An analyzer as in claim 4 together with means for permitting said attenuator means to move to a first position when substantially only specularly reflected energy is being received by the means responsive to ultraviolet light.

6. A surface analyzer as in claim 5 wherein said means permitting said attenuator means to move consists of spring means yieldably urging the attenuator means from a second to a first position and means connected to the attenuator means for retaining the same in a first position against the force of the spring when only substantially scattered energy is being collected.

7. In an analyzer for analyzing the surface of an object which is substantially opaque to ultraviolet light, a substantially light-tight housing having aperture means therein for viewing the surface of the object to be analyzed, illuminator means carried by the housing including a source of ultraviolet light and optical imaging means for directing light from the source through the aperture means and onto the surface of the object to illuminate the surface of the object, collector means carried by the housing including means responsive to ultraviolet light, optical imaging means for receiving ultraviolet light from said surface through said aperture means and directing it onto the means responsive to ultraviolet light, means carried by the housing permitting relative tilting movement between the surface of the object and the housing so that substantially only scattered reflected ultraviolet light is collected in one position of the housing and substantially only specularly reflected ultraviolet light is collected in a second position of the housing, the optical imaging means in the illuminator means and in the collector means each having two concave spherical mirrors used at 45° incidence angles.

8. An analyzer as in claim 7 wherein the optical imaging means of the illuminator and the collector means each has at least one folding mirror used at 45° incidence angle.

9. An analyzer as in claim 7 wherein the mirrors have reflecting surfaces provided with coatings that preferentially reflect ultraviolet light.

10. An analyzer as in claim 9 where said coating is a high reflector consisting of alternating layers of high and low index materials arranged in a quarterwave stack for 253.7 nm with a design angle of 45°.

11. An analyzer as in claim 10 where said high and low index materials are scandium oxide and silica.

12. An analyzer as in claim 7 wherein the concave mirrors of the illuminator means and the collector means closest to the aperture means have optical axes which are offset by 45°.

13. In an analyzer for analyzing the surface of an object which is substantially opaque to ultraviolet light, a substantially light-tight housing having aperture means therein for viewing the surface of the object to be analyzed, illuminator means carried by the housing including a source of ultraviolet light and optical imaging means for directing light from the source through the aperture means and onto the surface of the object to illuminate the surface of the object, collector means carried by the housing including means responsive to ultraviolet light, optical imaging means for receiving ultraviolet light from said surface through said aperture means and directing it onto the means responsive to ultraviolet light, means carried by the housing permitting relative tilting movement between the surface of the object and the housing so that substantially only scattered reflected ultraviolet light is collected in one position of the housing and substantially only specularly reflected ultraviolet light is collected in a second position of the housing, said means responsive to ultraviolet light being a photomultiplier tube and means for demodulating the signal from said photomultiplier tube at a predetermined frequency.

14. An analyzer as in claim 13 wherein said frequency is 120 Hertz.

15. In an analyzer for analyzing the surface of an object which is substantially opaque to ultraviolet light, a substantially light-tight housing having aperture means therein for viewing the surface of the object to be analyzed, illuminator means carried by the housing including a source of ultraviolet light and optical imaging means for directing light from the source through the aperture means and onto the surface of the object to illuminate the surface of the object, collector means carried by the housing including means responsive to ultraviolet light, optical imaging means for receiving ultraviolet light from said surface through said aperture means and directing it onto the means responsive to ultraviolet light, means carried by the housing permitting relative tilting movement between the surface of the object and the housing so that substantially only scattered reflected ultraviolet light is collected in one position of the housing and substantially only specularly reflected ultraviolet light is collected in a second position of the housing, said means carried by the housing including means for permitting tilting movement of the housing relative to the surface of the object being examined.

16. In an ultraviolet analyzer for evaluating a surface of an object by measuring ultraviolet light reflectivity scattered off of the surface, a housing, illuminator means carried by said housing including an ultraviolet light source, first optical imaging and filtering means having a plurality of reflecting surfaces for performing sequential imaging and filtering functions and passing ultraviolet light of a selected wavelength from the ultraviolet light source onto said surface, and collector means carried by said housing including detector means responsive to ultraviolet light, second optical imaging and filtering means having a plurality of reflecting surfaces for performing sequential imaging and filtering functions and passing ultraviolet light of said selected wavelength from said surface to said detector means, both of said first and second optical imaging and filtering means being folded and providing an effective aperture in the range of at least approximately 0.2 to 0.3 and filtering of at least two orders of magnitude.

17. An analyzer as in claim 16, wherein said detector means is a solar-blind photomultiplier tube.

18. An analyzer as in claim 16, wherein said ultraviolet light source is a low-pressure mercury vapor lamp with strong emission at 253.7 nm.

19. An analyzer as in claim 16, wherein said selected wavelength is 253.7 nm.

20. In an ultraviolet analyzer, a housing, illuminator means carried by said housing including an ultraviolet light source, optical imaging and filtering means having reflecting surfaces for performing the imaging and filtering functions and passing ultraviolet light of a selected wavelength from the ultraviolet light source onto said surface, and collector means carried by said housing including detector means responsive to ultraviolet light, optical imaging and filtering means having reflecting surfaces for performing the imaging and filtering functions and passing ultraviolet light of said selected wavelength from said surface to said detector means, both of said optical imaging and filtering means being folded and providing an effective aperture in the range of approximately 0.2 to 0.3 and filtering of at least two orders of magnitude, the optical imaging and filtering means in the illuminator means and in the collector means each having two concave spherical mirrors used at 45° incidence angles.

21. An analyzer as in claim 20, wherein the optical imaging and filter means each have at least one folding mirror used at 45° incidence angle.

22. An analyzer as in claim 20, wherein the mirrors have reflecting surfaces with coatings that preferentially reflect a selected wavelength of ultraviolet light.

23. An analyzer as in claim 22, wherein each coating is a high reflector consisting of alternating layers of high and low-index materials arranged in a quarterwave stack for the selected wavelength of ultraviolet light with a design angle of 45°.

24. An analyzer as in claim 23, wherein said high and low-index materials are scandium oxide and silica.

25. An analyzer as in claim 20, wherein the concave mirrors of the illuminator and the collector means closest to said surface have their optical axes offset by 45°.

26. In an analyzer for evaluating a surface of an object by measuring ultraviolet light reflectivity scattered off of the surface, a housing, illuminator means carried by said housing including an ultraviolet light source, optical imaging and filter means for passing ultraviolet light of a selected wavelength from the ultraviolet source onto said surface, and collector means carried by said housing including detector means responsive to ultraviolet light, optical imaging and filtering means having reflecting surfaces for performing the imaging and filtering functions and passing ultraviolet light of said selected wavelength from said surface to said detector means and means for causing substantially only scattered reflected ultraviolet light to be received by said detector means and alternatively substantially only specularly reflected light to be received by said detector means and means carried by the housing permitting relative tilting motion between surface of said object and housing between two fixed positions; the first position being such that substantially only specularly reflected ultraviolet light is collected by the collector means, the second position being such that substantially only scattered reflected ultraviolet light is collected by the collector means.

27. In a method for analyzing the surface of a glass object, directing ultraviolet light solely by reflection in a sequence of reflective steps onto the object to illuminate the surface and collecting ultraviolet light reflected from the surface at different angles solely by reflection in a sequence of reflective steps so that at one angle substantially only reflected specular ultraviolet light is collected and measured to provide a calibrated standared, and at another angle substantially only reflected scattered ultraviolet light is collected and measured, with both sequences of reflective steps providing an effective aperture in the range of at least approximately 0.2 to 0.3 and filtering of at least two orders of magnitude.

* * * * *